United States Patent [19]

Siegmeier et al.

[11] Patent Number: 4,605,795
[45] Date of Patent: Aug. 12, 1986

[54] CONTINUOUS PROCESS FOR THE PRODUCTION OF PENTANEDIOL-1,2

[75] Inventors: Rainer Siegmeier, Frankfurt; Günter Prescher, Hanau; Helmut Maurer, Rodenbach; Günter Hering, Alzenau, all of Fed. Rep. of Germany

[73] Assignee: Degussa Aktiengesellschaft, Frankfurt, Fed. Rep. of Germany

[21] Appl. No.: 798,798

[22] Filed: Nov. 15, 1985

[30] Foreign Application Priority Data

Nov. 24, 1984 [DE] Fed. Rep. of Germany ....... 3442937

[51] Int. Cl.⁴ .................. C07C 29/00; C07C 31/20
[52] U.S. Cl. ................................................. 568/867
[58] Field of Search .............................. 568/867

[56] References Cited

U.S. PATENT DOCUMENTS

| 3,475,499 | 10/1969 | Winnick | 260/615 |
| 3,991,126 | 11/1976 | Bacskai | 568/867 |
| 4,390,738 | 6/1983 | Waddan et al. | 568/867 |

FOREIGN PATENT DOCUMENTS 0062234  4/1982  Japan ................................. 568/867

Primary Examiner—J. E. Evans
Attorney, Agent, or Firm—Cushman, Darby & Cushman

[57] ABSTRACT

There is provided a process for the continuous production of pentanediol-1,2 comprising epoxidizing pentene in a completely homogeneous phase with perpropionic acid in benzene to 1-pentene oxide and directly saponifying the pentene oxide-1 without isolation. High yields and a high degree of purity of pentanediol-1,2 are obtained.

20 Claims, 2 Drawing Figures

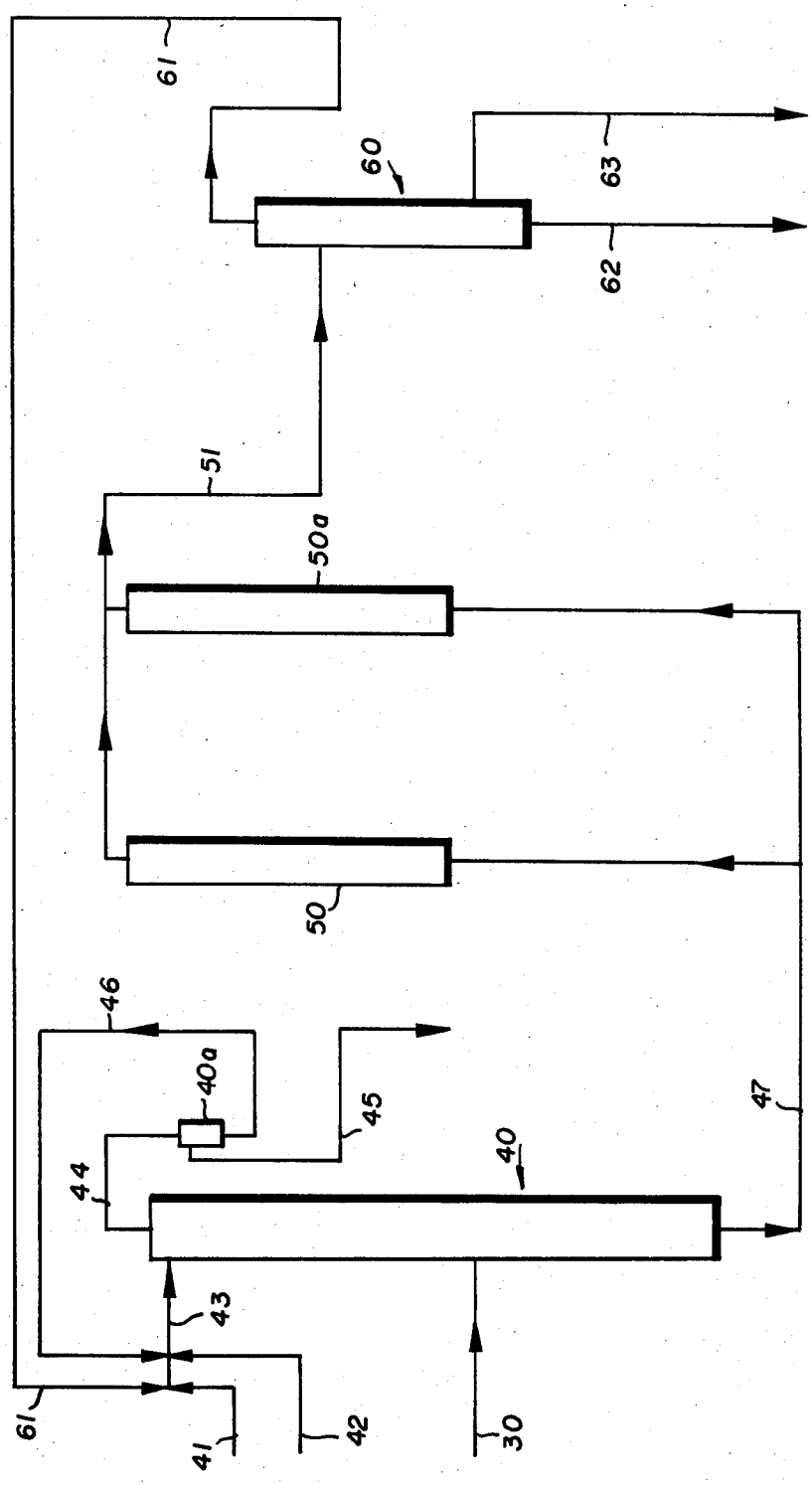

CONTINUOUS PROCESS FOR THE PRODUCTION OF PENTANEDIOL-1,2

BACKGROUND OF THE INVENTION

The invention is directed to the continuous production of pentanediol-1,2 from pentene by oxidizing it to pentene oxide-1,2 and saponifying this epoxide with water to form pentanediol-1,2.

Pentanediol-1,2 is useful as an intermediate in the production of fungicides.

Mention of the production of pentanediol-1,2 is found, e.g., in German patent No. 2,205,023 which describes a one-step process for the simultaneous expoxidation and saponification of higher olefins, i.e., olefins, which preferably should have at least 4 carbon atoms. This one-step process uses aqueous percarboxylic acid solutions, both for the epoxidation and the saponification. However, there is required considerable amounts of water, which is particularly expensive in carrying out the process.

According to U.S. Pat. No. 3,475,499, there is described a two-step process for the production of 1,2-epoxides and saponification to the corresponding diols in which the epoxidation can be carried out continuously with hydroperoxides in the presence of organic solvents such as hydrocarbons. However, these hydrocarbons should be distilled off, preferably before the saponification.

According to this patent, the epoxide containing sump resulting from the distillation of the epoxidation mixture is saponified with water in the presence of alkaline or acid catalysts. According to Example 1 which is directed to a $C_{11}-C_{15}$-olefin cut the yield of epoxide is only 45%; it is saponified together with the unreacted olefin.

Although the selectivity is higher thereby the amount of pure diol, due to the low yield of epoxide, is moderate and is industrially non-interesting.

Thus, it is the task of the invention to develop a low cost industrial continuous process for the production of pentanediol-1,2 by epoxidizing pentene-1,2 and subsequent saponification of the resulting epoxide in aqueous medium with an industrially satisfactory yield and with very good selectivity.

SUMMARY OF THE INVENTION

It has now been found that this problem can be solved by in a first step reacting pentene with a benzene solution of perpropionic acid, in which optionally propionic acid is still present, at a mole ratio of pentane to perpropionic acid such as 0.5 to 5:1 at a temperature of 20° to 110° C. and a pressure of 1 to 10 bar, fractionally distilling the epoxidation mixture and returning the most volatile fraction, which chiefly consists of pentene, into the epoxidation with the perpropionic acid solution, introducing the middle volatile fraction, which chiefly consists of pentene oxide and benzene, into the middle of a saponification column, saponifying it there with a sufficient amount of water for the saponification of the pentene oxide in the presence of an acid catalyst at 30° to 150° C., preferably at 60° to 80° C., as well as at 1 to 5 bar, drawing off overhead a benzene-water mixture, separating this mixture into water, which is returned to the saponification column, and benzene and drawing off at the bottom of the column pentanediol-1,2 in aqueous acid solution and withdrawing the least volatile fraction at the bottom of the fractionating column for the epoxidation mixture.

In general, the perpropionic acid solution in benzene contains 10 to 30 weight percent perpropionic acid, preferably 20 weight percent.

It is very convenient to employ as pentene the commercial pentene having a content of pentene-1 of 96%; in case it is desired there can also be used pentene having a higher or lower content of pentene-1. Pentene is preferably added in liquid phase under a slight superatmospheric pressure.

The preferred mole ratio of pentene to perpropionic acid is between 0.7 to 5:1, above all at 1 to 3:1.

There have proven convenient temperatures of 20° to 100° C., above all of 55° to 60° C., likewise pressure of 1 to 2 bar.

The epoxidation is carried out in known reactors, preferably in two reactors connected in succession. If it should be necessary, a subsequent reactor can be connected. There can be used as reactors the customary stirring vessels, tubular reactors, or loop reactors. As is known, a quick separation of epoxide and the carboxylic acid formed is very desirable. Therefore, the epoxidation mixture is separated by distillation into three fractions:

The most volatile fraction, which chiefly consists of pentene is returned to the epoxidation, the middle volatile fraction is chiefly pentene oxide in benzene and is further treated in the saponification step, while the least volatile fraction consists of propionic acid and high boiling by-products. A further separation into propionic acid and the by-products, e.g., by working up through distillation, and return of the propionic acid to the production of perpropionic acid is possible.

The fractional distillation of the epoxidation mixture can be carried out in a single column. However, it is especially favorable to operate in two stage steps, thus in two columns, which are connected in succession, and to further fractionate in a second column the most volatile fraction of the first column, which chiefly consists of pentene, pentene oxide, and benzene. The sump fraction of the second column then is led into the saponification step.

There can be used as columns for the distillation of the epoxide mixture as well as for the saponification customary distillation columns, which preferably are operated at atmospheric pressure, superatmospheric pressure, or reduced pressure (i.e., a vacuum).

This sump fraction chiefly of pentene oxide and benzene is introduced into the middle of the saponification column and the water, which contains the acid catalyst delivered near the head of the column. The mixture of benzene and water drawn off at the head in the distillation is an azeotrope containing 91 weight percent benzene, which boils at 69° C.

Thus, the water supplied to the column serves not only to saponify the pentene oxide but also simultaneously to remove the benzene. Thus, there must be present at least as much water as will be able to fulfill these two requirements.

It has been found that a benzene-water ratio of 5:1 to 1:1 parts by weight is quite favorable. A ratio of 1.5 to 2:1 parts by weight is very suitable.

If the amount of water is also set based on the amount of pentene oxide to be saponified, then here also it has proven good to use amounts of 1 to 5 parts by weight water to 1 part by weight pentene oxide-1,2.

The azeotrope passing over at the head of the column is separated into benzene and water, of which the water is returned directly into the saponification column, the benzene—if desired—into the production of the benzene solution of perpropionic acid or eventually into the epoxidation.

The acid catalyst is present in an amount of 0.05 to 5 weight percent in water. The materials used as acid catalysts are known for this purpose. There can be used both inorganic and organic compounds. Thus, there can be used mineral acids as well as organic acids. Among the mineral acids, there are preferred sulfuric acid, hydrochloric acid, or ortho phosphoric acid, among the organic acids formic acid, acetic acid, or propionic acid as well as isobutyric acid or methanesulfonic acid. Sulfuric acid is especially preferred.

The pentanediol-1,2 in aqueous acid solution as sump of the saponification column is preferably subjected to a post treatment by neutralization and subsequent distillation. The neutralization, for example, can be carried out with the help of a basic ion exchanger; the neutralized pentanediol obtained thereby is fractionally distilled to remove water and high boiling by-products and withdrawn from the distillation column as a side stream in highly purified form. The water resulting as head product thereby can be supplied to the saponification step.

BRIEF DESCRIPTION OF THE DRAWINGS

FIG. 2 is a diagrammatic illustration of the saponification of the epoxide solution and the production of the pure product.

Figure 1:
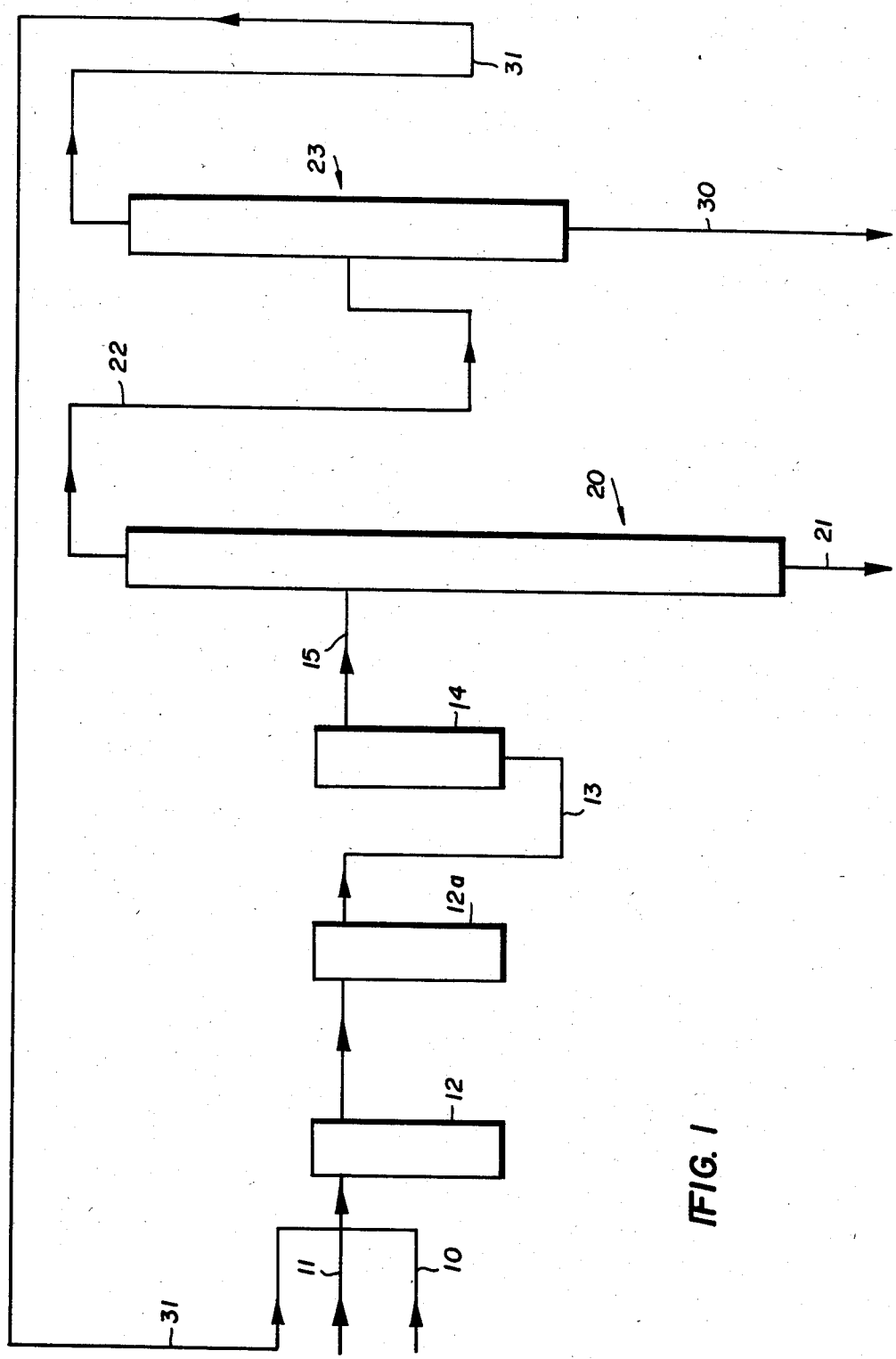
FIG. 1 is a diagrammatic illustration of the epoxidation of pentene with a benzene solution of perpropionic acid as well as working up of the epoxidation mixture.

The process can comprise, consist essentially of, or consist of the stated steps with the recited materials.

DETAILED DESCRIPTION

The plant consists of two reactors 12 and 12a which are charged with a solution of perpropionic acid in benzene via line 10 and with fresh pentene via line 11 as well as recycle pentene via the return line 31. In case it is necessary, the reaction mixture is supplied via a line 13 to a further reactor 14. The reaction mixture is supplied from reactor 12a or further reactor 14 to a distillation column 20. A difficultly volatile fraction is drawn off from this column via line 21. The fraction consists of propionic acid and high boiling by-products.

The lower boiling fraction of distillation column 20 is fed via the line 22 into a second distillation column 23. The lower boiling fraction of the column 23, which contains pentene exclusively, is supplied via the return line 31 to the reactors 12 and 12a. The less volatile fraction of the distillation column 23 contains almost exclusively pentene oxide and benzene. It is supplied via line 30 to step 2.

The solution of pentene oxide in benzene produced in step 1 is fed via line 30 into the middle of a distillation column 40. Via the line 41, fresh water, the lines 61 and 44 return water and via the line 42 sulfuric acid are fed together into the upper part of column 40 via line 43. The lower boiling fraction of the distillation column 40 consists of water, which is again supplied to the column via return line 44, and benzene, which is separated from the water in a separatory vessel 40a and can be withdrawn via the line 45. The less volatile fraction of the column 40, which consists chiefly of dilute sulfuric acid and pentanediol, is supplied via line 47 to the ion exchanger 50, which can be operated interchangeably. The solution is supplied from the exchanger 50 or 50a via the line 51 to a distillation unit 60. The lower boiling fraction, which almost exclusively contains water, is supplied via the return line 61 to the distillation column 40. The final product pentanediol-1,2 is drawn off in a side stream 63 in the lower part of the distillation unit 60. The high boiling waste products are withdrawn via the line 62.

The technological advantage of the fully continuous process of the invention first is in the possibility of carrying out the epoxidation in completely homogeneous phase at normal pressure or only a slight superatmospheric pressure, at which the boiling point of the solution is not reached, at high reaction and high selectivity. The epoxide formed thereby without isolation is subjected directly to the saponification and pentanediol obtained in very good yields based on the pentene; and secondly its high degree of purity. Generally, there is reached a perpropionic acid reaction of around 99% and epoxidation yields of about 93%, based on the reacted pentene. The yields in the saponification step for the quantitative epoxide reaction are, inter alia, at 99%. The final product pentanediol is obtained, inter alia, in a degree of purity of above 99%.

The saponification is carried out with substantially smaller amounts of water than according to the process of German patent No. 2205023. In contrast, moreover, according to the process of the invention, the reaction heat liberated in the saponification step is used for the simultaneous distillation of the benzene. Through this a portion of the necessary supply of energy is saved; therefore, there can be eliminated an additional separation step.

Besides a completely closed system is present, in which the charge or adjuvants such as pentene, propionic acid, benzene, and water are recycled and do not leave the system. The invention is explained in more detail in the following example (continuous procedure) and comparison example (discontinuous procedure).

EXAMPLE (CONTINUOUS)

In an experiment lasting 70 hours, there were fed into reactors 12 and 12a per hour 100 grams of fresh pentene and about 52 grams of recycle pentene as well as about 600 grams of a 20 weight percent solution of perpropionic acid in benzene. The reactors were held at a temperature of 55° to 60° C. and 1.0 bar. There left the post reactor 14 per hour about 753 grams of reaction mixture, which was separated in the distillation column 20 into 189 grams of propionic acid which still contained high boiling by-products, and 564 grams of the lower boiling fraction.

The lower boiling fraction was distilled again in column 23. There were drawn off overhead about 52 grams of recycle pentene which was led back via line 31 into the reactors 12 and 12a. The sump product, which consisted almost exclusively of pentene oxide and benzene (512 grams), was supplied in step 2 via line 30 to the column 40. There was dosed into this in the upper part via line 43 in all 214 grams of water which contained 0.1 weight percent of sulfuric acid. There were drawn off hourly overhead, via line 44, 381 grams of benzene as well as 34 grams of water, in the separatory vessel 40a these were separated into benzene which was drawn off via line 45 and into water which was returned via line 46 into line 43 and column 40.

There accumulated in the sump of the column 40 about 288 grams of an aqueous solution of pentanediol which still contained sulfuric acid (about 0.07 weight percent). This acid solution was neutralized in the ion exchangers 50 or 50a and subsequently distilled in column 60. There were obtained per hour 130 grams of pentanediol and 154 grams of water, the water was again supplied to the column 40 via line 61. After the first step pentene oxide was present in a yield of 93.6% based on the pentene reacted. The saponification yield in step 2 was 99% based on the epoxide employed. The purity of the final product was 99.2%.

As ion exchangers, there can be used basic ion exchangers, e.g., crosslinked polystyrene with trialkylammonium groups, e.g., styrene-divinyl benzene copolymer haing trimethylammonium groups attached or phenol-formaldehyde condensate with alkylamines, e.g., dimethylamine or with diethylenetriamine.

In this example was used an ion exchanger consisting of Lewatit M 600.

COMPARISON EXAMPLE (DISCONTINUOUS)

There were present in a three-necked flask (1000 ml) equipped with an internal thermometer and reflux condenser 112 grams of pentene oxide, 224 grams of water, and 397 grams of benzene, and this was treated with 0.1 weight percent sulfuric acid based on the water employed and heated to boiling.

After a reaction time of 8 hours, there were ascertained titrimetrically and by gas chromatograph the epoxide reaction, the yield and the amount of high boiling by-products.

Based on the pentene oxide employed, the yield was 88% and the purity was 92.8%.

The entire disclosure of German priority application No. P3442937.9 is hereby incorporated by reference.

What is claimed is:

1. A continuous process for the production of pentanediol starting from pentene, oxidizing it to pentene oxide-1,2 using perpropionic acid and saponification of the epoxide with water at moderate temperature and moderate pressure comprising in a first step reacting pentene with a solution of perpropionic acid or a mixture of perpropionic acid and propionic acid in benzene at a mole ratio of pentene to perpropionic acid of 0.5 to 5:1 at a temperature of 20° to 110° C. and a pressure of 1 to 10 bar, fractionally distilling the epoxidation mixture in a fractionating column, returning the most volatile fraction, which consists chiefly of pentene, into the epoxidation with perpropionic acid solution, supplying the intermediately volatile fraction, which consists chiefly of pentene oxide and benzene, into the middle of a saponification column, in a second step saponifying it there with a sufficient amount of water to saponify the pentene oxide and in the presence of an acid catalyst at 30° to 150° C. and at 1 to 5 bar, withdrawing overhead a benzene-water mixture, separating this mixture into water and benzene, returning the separated water to the saponification column, at the bottom of the saponification column drawing off pentanediol-1,2 in aqueous acid, and withdrawing the least volatile fraction from the bottom of the fractionating column.

2. A process according to claim 1 wherein the saponification is carried out at 60° to 80° C.

3. A process according to claim 1 wherein there is employed in the first step a 10 to 30 weight percent solution of perpropionic acid in benzene.

4. A process according to claim 3 wherein the pentene to perpropionic acid ratio is 0.7 to 5:1.

5. A process according to claim 4 wherein the ratio of pentene is perpropionic acid is 1 to 3:1.

6. A process according to claim 1 wherein the pentene to perpropionic acid ratio is 0.7 to 5:1.

7. A process according to claim 5 wherein in the first step the temperature is 20° to 100° C. and the pressure 1.0 to 2 bar.

8. A process according to claim 1 wherein in the first step the temperature is 20° to 100° C. and the pressure 1.0 to 2 bar.

9. A process according to claim 7 comprising separating the epoxidation mixture from pentene and perpropionic acid in two steps, wherein in a first distillation column there is separated a high boiling fraction consisting of propionic acid and by-products and a more volatile fraction consisting of pentene, pentene oxide, and benzene and then in a second distillation column this more volatile fraction is separated into pentene and a mixture of pentene oxide, and benzene returning the pentene to the reaction step and introducing the mixture of pentene oxide and benzene into the saponification column.

10. A process according to claim 1 comprising separating the epoxidation mixture from pentene and perpropionic acid in two steps, wherein in a first distillation column there is separated a high boiling fraction consisting of propionic acid and by-products and a more volatile fraction consisting of pentene, pentene oxide, and benzene and then in a second distillation column this more volatile fraction is separated into pentene and a mixture of pentene oxide, and benzene returning the pentene to the reaction step and introducing the mixture of pentene oxide and benzene into the saponification column.

11. A process according to claim 9 wherein in the saponification there is used 1 to 5 parts by weight of water containing 0.05 to 5 weight percent of an acid catalyst per part by weight of pentene oxide-1,2.

12. A process according to claim 10 wherein in the saponification there is used 1 to 5 parts by weight of water containing 0.05 to 5 weight percent of an acid catalyst per part by weight of pentene oxide-1,2.

13. A process according to claim 1 wherein in the saponification there is used 1 to 5 parts by weight of water containing 0.05 to 5 weight percent of an acid catalyst per part by weight of pentene oxide-1,2.

14. A process according to claim 11 wherein the saponification is carried out in a medium containing benzene and water in a ratio between 5:1 and 1:1.

15. A process according to claim 13 wherein the saponification is carried out in a medium containing benzene and water in a ratio between 5:1 and 1:1.

16. A process according to claim 10 wherein the saponification is carried out in a medium containing benzene and water in a ratio between 5:1 and 1:1.

17. A process according to claim 14 wherein the acid catalyst is sulfuric acid, hydrochloric acid, or phosphoric acid.

18. A process according to claim 1 wherein the acid catalyst is sulfuric acid, hydrochloric acid, or phosphoric acid.

19. A process according to claim 14 wherein the acid catalyst is formic acid, acetic acid, propionic acid, isobutyric acid, or toluenesulfonic acid.

20. A process according to claim 1 wherein the acid catalyst is formic acid, acetic acid, propionic acid, isobutyric acid, or toluenesulfonic acid.

* * * * *